United States Patent
Nita et al.

(10) Patent No.: US 9,770,250 B2
(45) Date of Patent: Sep. 26, 2017

(54) ULTRASOUND CATHETER FOR DISRUPTING BLOOD VESSEL OBSTRUCTIONS

(71) Applicant: FLOWCARDIA, INC., Tempe, AZ (US)

(72) Inventors: Henry Nita, Redwood Shores, CA (US); Jeff Sarge, Fremont, CA (US); Martinos Tran, Tracy, CA (US); Simon Nguyen, San Jose, CA (US)

(73) Assignee: Flowcardia, Inc., Sunnyvale, CA (US)

( * ) Notice: Subject to any disclaimer, the term of this patent is extended or adjusted under 35 U.S.C. 154(b) by 0 days.

(21) Appl. No.: 15/098,984

(22) Filed: Apr. 14, 2016

(65) Prior Publication Data

US 2016/0242797 A1 Aug. 25, 2016

Related U.S. Application Data

(60) Continuation of application No. 14/244,247, filed on Apr. 3, 2014, now Pat. No. 9,314,258, which is a
(Continued)

(51) Int. Cl.
*A61B 17/20* (2006.01)
*A61B 17/22* (2006.01)
(Continued)

(52) U.S. Cl.
CPC ........ *A61B 17/22* (2013.01); *A61B 17/22012* (2013.01); *A61M 37/0092* (2013.01);
(Continued)

(58) Field of Classification Search
CPC .............. A61B 17/22012; A61B 17/22; A61B 2017/00477; A61B 2017/22015;
(Continued)

(56) References Cited

U.S. PATENT DOCUMENTS 5,342,292 A * 8/1994 Nita ................. A61B 17/22012
604/22
5,542,917 A * 8/1996 Nita ................. A61B 17/22012
601/3

* cited by examiner

*Primary Examiner* — Jason Flick
(74) *Attorney, Agent, or Firm* — C.R. Bard Intellectual Property Buchalter

(57) ABSTRACT

Ultrasound catheter devices and methods provide enhanced disruption of blood vessel obstructions. Generally, an ultrasound catheter includes an elongate flexible catheter body with one or more lumens. An ultrasound transmission member or wire extends longitudinally through the catheter body lumen and, in many embodiments, a guide wire tube also extends through the same lumen. A distal head is fixed to or otherwise mechanically coupled with the distal end of the ultrasound transmission member or wire and is positioned adjacent the distal end of the catheter body. Although the distal end of the catheter body overlaps the distal head, the distal head is not directly affixed to the distal end of the catheter body. Thus, the distal tip may move freely, relative to the distal end of the catheter body when ultrasonic energy is applied through the ultrasound transmission member. Such a freely floating distal head enhances the efficiency of an ultrasound catheter, enabling the catheter to ablate calcific occlusions and increasing the useful life of the ultrasound transmission member and catheter.

19 Claims, 7 Drawing Sheets

Related U.S. Application Data continuation of application No. 13/673,848, filed on Nov. 9, 2012, now Pat. No. 8,690,819, which is a continuation of application No. 13/153,359, filed on Jun. 3, 2011, now Pat. No. 8,308,677, which is a continuation of application No. 11/466,738, filed on Aug. 23, 2006, now Pat. No. 7,955,293, which is a division of application No. 10/229,371, filed on Aug. 26, 2002, now Pat. No. 7,137,963.

(51) Int. Cl.
*A61M 37/00* (2006.01)
*A61B 17/00* (2006.01)
*A61B 17/32* (2006.01)

(52) U.S. Cl.
CPC ........ *A61B 2017/00477* (2013.01); *A61B 2017/22015* (2013.01); *A61B 2017/22018* (2013.01); *A61B 2017/22038* (2013.01); *A61B 2017/320072* (2013.01); *A61B 2017/320084* (2013.01)

(58) Field of Classification Search
CPC ......... A61B 2017/22018; A61B 2017/320072; A61B 2017/320084; A61B 17/2202; A61B 2017/22038; A61B 2017/320088; A61B 2017/22039; A61B 17/320068; A61B 2019/5276; A61B 17/00234; A61B 17/22004; A61B 8/12; A61B 5/0084; A61B 2017/22014; A61M 37/0092; A61M 2205/058; A61N 7/00
USPC .......................................................... 604/22
See application file for complete search history.

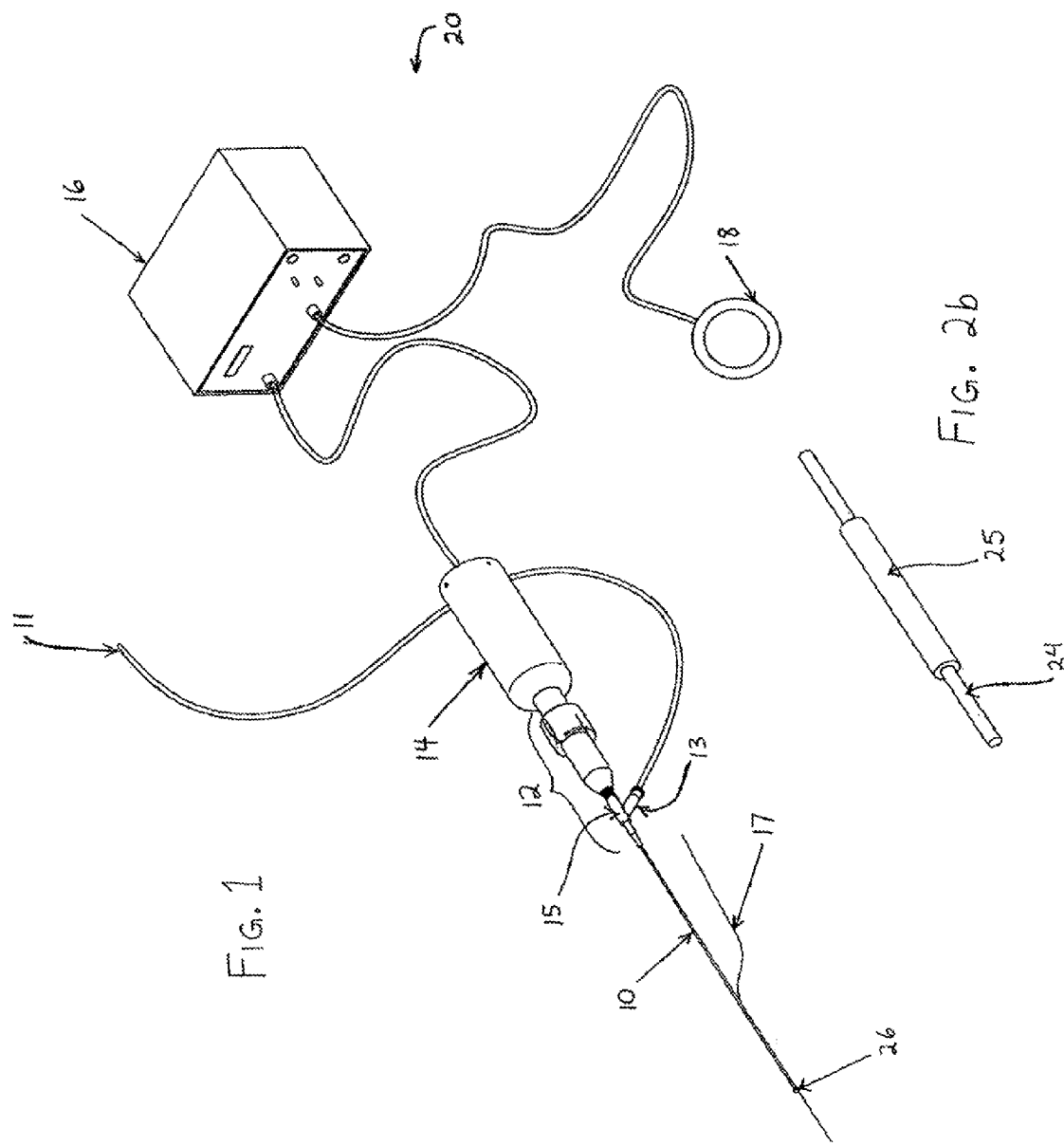

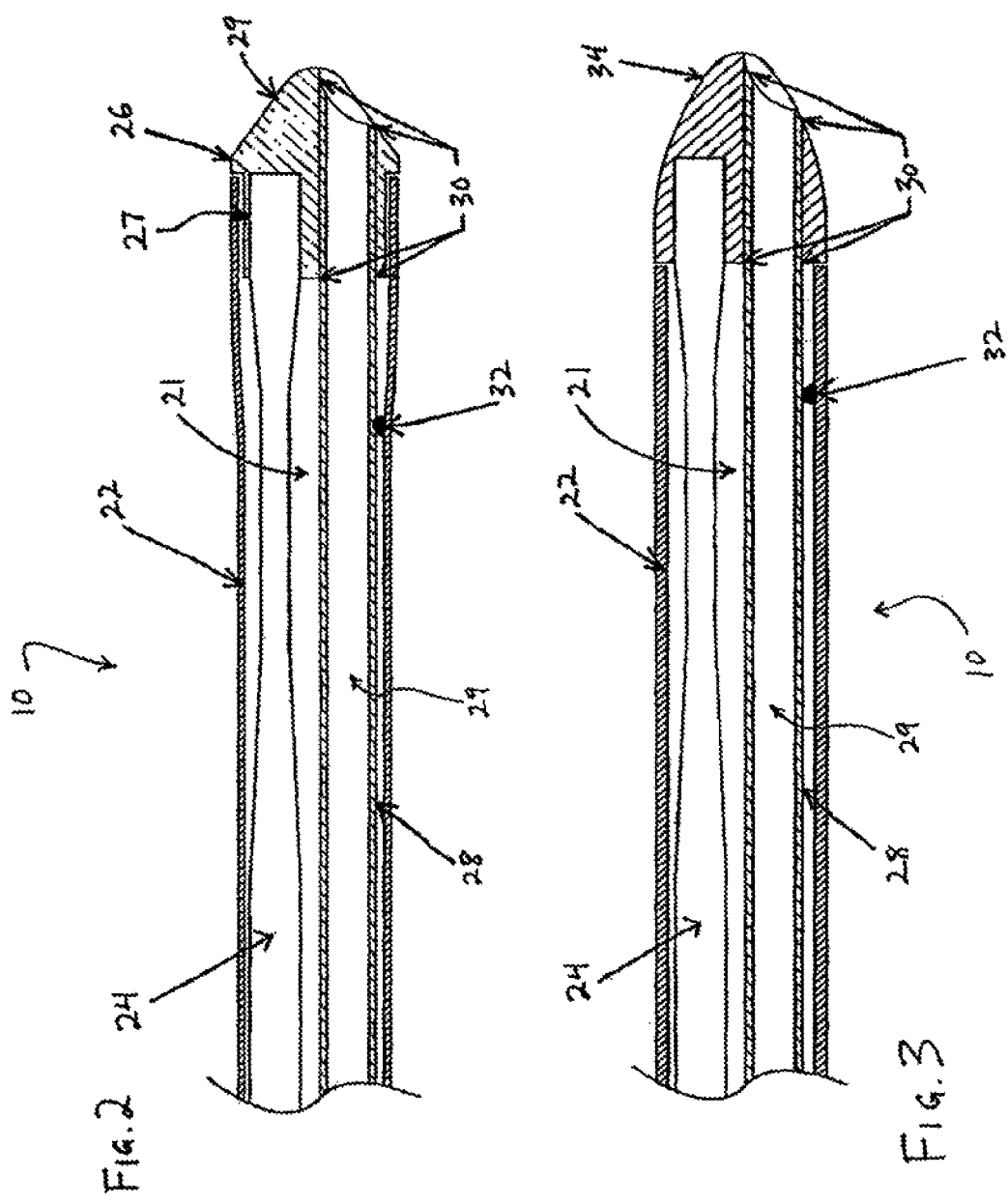

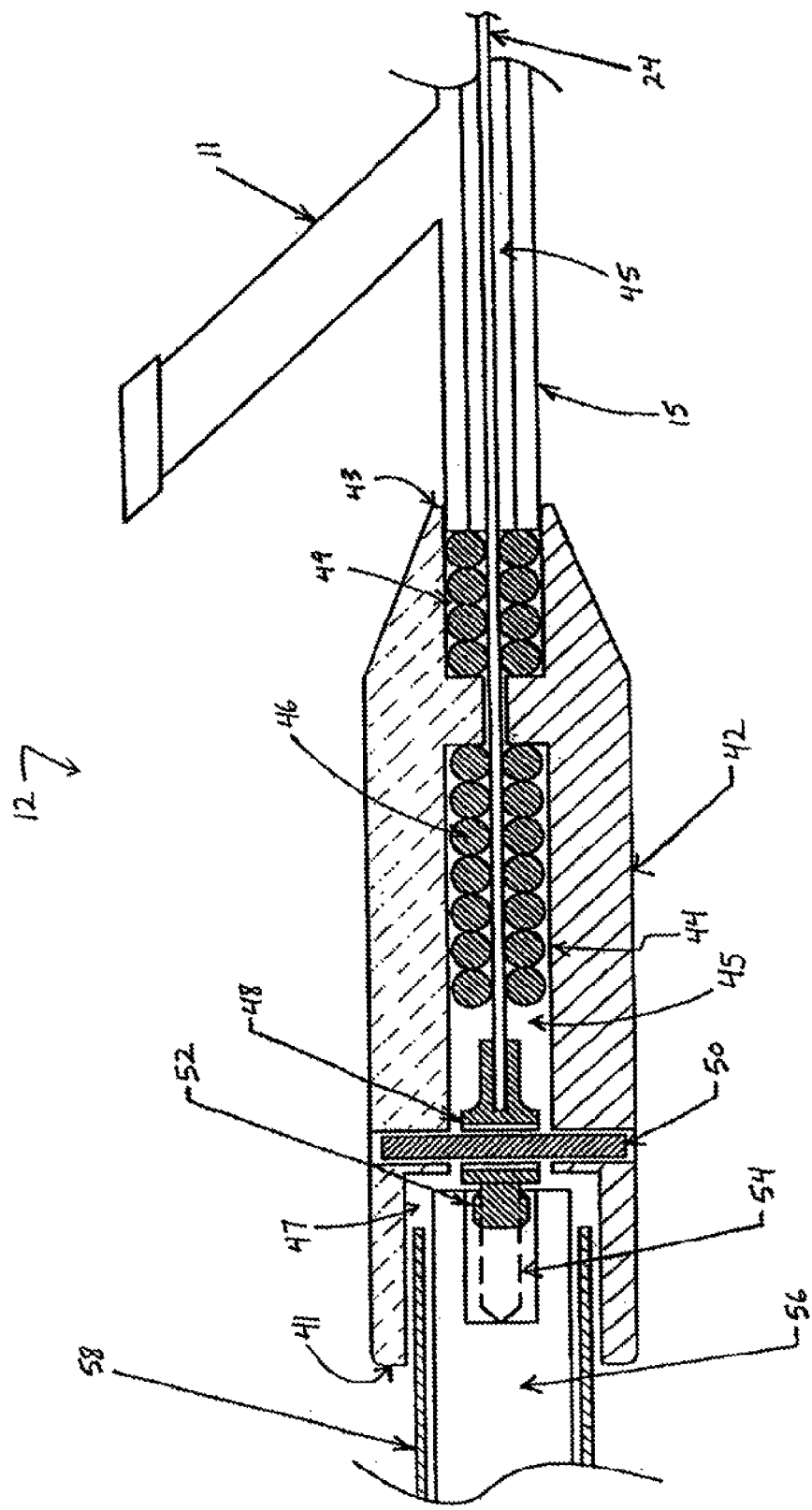

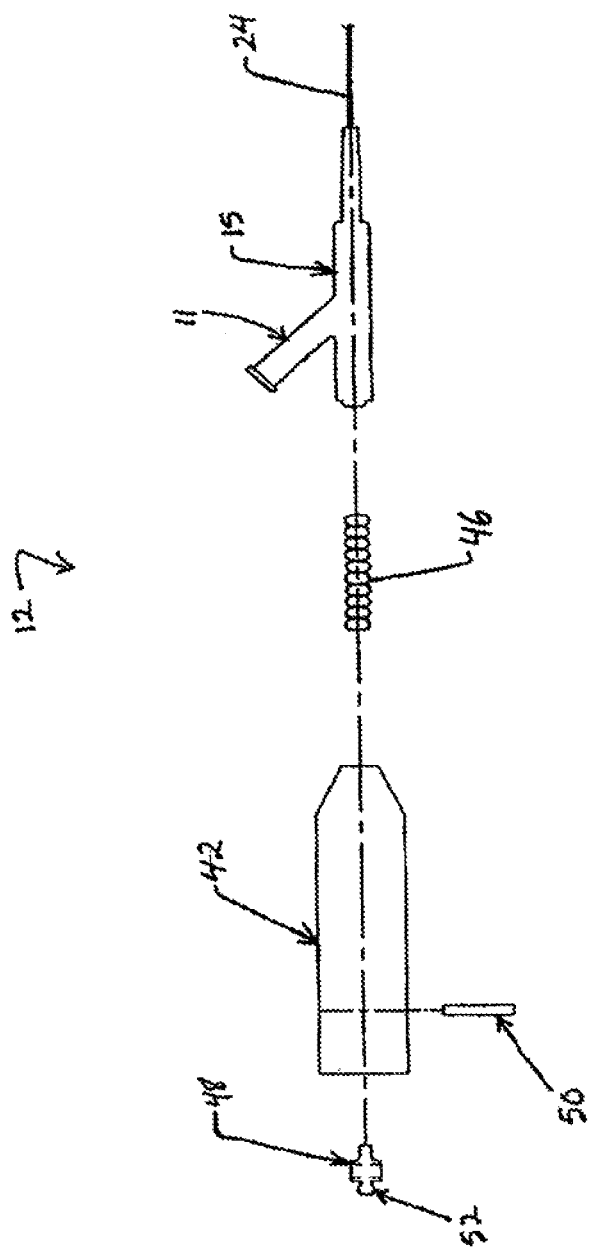

ULTRASOUND CATHETER FOR DISRUPTING BLOOD VESSEL OBSTRUCTIONS

CROSS-REFERENCE TO RELATED APPLICATIONS

This application is a continuation application of application Ser. No. 14/244,247, filed Apr. 3, 2014, now U.S. Pat. No. 9,314,258, which is a continuation of application Ser. No. 13/673,848, filed on Nov. 9, 2012, now U.S. Pat. No. 8,690,819, which is a continuation of Ser. No. 13/153,359, filed on Jun. 3, 2011, now U.S. Pat. No. 8,308,677, which is a continuation of application Ser. No. 11/466,738, filed on Aug. 23, 2006, now U.S. Pat. No. 7,955,293, which is a divisional of application Ser. No. 10/229,371, filed Aug. 26, 2002, now U.S. Pat. No. 7,137,963, all of which are hereby expressly incorporated by reference in their entireties.

BACKGROUND OF THE INVENTION

The present invention relates generally to medical devices and methods. More specifically, the present invention relates to ultrasound catheter devices and methods for treating occlusive intravascular lesions.

Catheters employing various types of ultrasound transmitting members have been successfully used to ablate or otherwise disrupt obstructions in blood vessels. Specifically, ablation of atherosclerotic plaque or thromboembolic obstructions from peripheral blood vessels such as the femoral arteries has been particularly successful. To disrupt occlusions of small blood vessels, such as the coronary arteries, ultrasound catheters must typically be sufficiently small and flexible to permit their advancement through the tortuous vasculature of the aortic arch, coronary tree, or other similarly narrow vasculature. Thus, safely and effectively disrupting or ablating obstructions from coronary arteries with ultrasound energy devices depends largely on the diameter and flexibility of the ultrasound catheter employed.

Various ultrasonic catheter devices have been developed for use in ablating or otherwise removing obstructive material from blood vessels. For example, U.S. Pat. Nos. 5,267,954 and 5,380,274, issued to the inventor of the present invention and hereby incorporated by reference, describe ultrasound catheter devices for removing occlusions. Other examples of ultrasonic ablation devices for removing obstructions from blood vessels include those described in U.S. Pat. No. 3,433,226 (Boyd), U.S. Pat. No. 3,823,717 (Pohlman, et al.), U.S. Pat. No. 4,808,153 (Parisi), U.S. Pat. No. 4,936,281 (Stasz), U.S. Pat. No. 3,565,062 (Kuris), U.S. Pat. No. 4,924,863 (Sterzer), U.S. Pat. No. 4,870,953 (Don Michael, et al), and U.S. Pat. No. 4,920,954 (Alliger, et al.), as well as other patent publications W087-05739 (Cooper), W089-06515 (Bernstein, et al.), W090-0130 (Sonic Needle Corp.), EP, EP316789 (Don Michael, et al.), DE3,821,836 (Schubert) and DE2438648 (Pohlman). While many ultrasound catheters have been developed, however, improvements are still being pursued.

Typically, an ultrasound catheter transmits energy from an ultrasound transducer through a transducer horn and then a transmission member, such as a wire, to a distal head. Ultrasound energy propagates through the transmission member as a sinusoidal wave to cause the distal head to vibrate. Such vibrational energy is typically utilized to ablate or otherwise disrupt vascular obstructions. To effectively reach various sites for treatment of intravascular occlusions, such ultrasound catheters often have lengths of about 150 cm or longer.

One difficulty related to transmission of ultrasound energy through long catheters is premature wear and tear and breakage of the catheter body, the ultrasound transmission member, or both. In general, an ultrasound transmission member or wire must be flexible enough to be passed through various areas of the cardiovascular circulation, but must also have sufficient strength to transmit energy to the catheter tip to ablate vascular obstructions. A stronger, more durable transmission wire allows for greater transmission of energy and is more durable than a thinner wire, but it may not be flexible or thin enough to be advanced through the vasculature to a desired treatment area. A thinner wire is less durable and more susceptible to breakage.

Currently available ultrasonic transmission wires typically break toward the distal end of the ultrasound wire, where the cross-sectional area of the wire becomes smaller. Wire breakage is generally caused by stress concentration due to transverse vibrations and fatigue. When ultrasonic energy is conveyed through the transmission member to the distal head, the head vibrates in both a longitudinal direction (back and forth in the direction of the longitudinal axis of the catheter) and a transverse direction (back and forth perpendicular to the longitudinal axis of the catheter). The longitudinal vibrations typically create the beneficial effects of disrupting an occlusion, while the transverse vibrations are predominantly unwanted artifact that stresses and fatigues the transmission member. One goal in developing ultrasound catheters, therefore, is to dampen transverse vibration of the transmission member while still providing an optimal level of longitudinal motion.

One proposed solution for limiting transverse vibration to prevent wire breakage in ultrasound catheters is to place one or more transverse vibration absorbers near the distal end of the wire or around the smallest cross-sectional area of the catheter, near its distal end. Such a solution is significantly limited, however, by the structural requirements of an ultrasound catheter. Typically, an ultrasound catheter is a small, single lumen tube, which requires continuous irrigation to cool the wire while ultrasound energy is delivered. Placing one or more vibration absorbers at or near the distal end typically increases the diameter of the catheter, interferes with the continuous irrigation system, or both.

Several prior patents describe such transverse vibration absorbers. For example, U.S. U.S. Pat. No. 5,397,293 (Alliger et al.), hereby incorporated by reference, and U.S. Pat. Nos. 5,380,274 and 5,267,954, previously incorporated herein by reference, describe catheter devices having a distal head affixed to the catheter body. Affixing the head to the catheter body acts to limit transverse motion of the head. With such an affixed distal head, however, more ultrasound energy is required to produce a desired amount of longitudinal vibration to disrupt or ablate a vascular occlusion. Ironically, increasing the ultrasound energy applied to the transmission wire may actually cause increased stress on the wire and, consequently, premature wire fatigue and breakage.

Another challenge in developing ultrasound catheters is to provide sufficient mechanical energy at the distal head to break through calcified plaque. Intravascular plaque is often composed of calcified material so hard that treatment devices typically cannot pass through them. At the present time, neither ultrasound catheters nor any other comparable devices have solved the problem of calcific plaque occlusions in blood vessels.

Therefore, a need exists for ultrasound catheter devices and methods that allow for ablation or disruption of vascular occlusions, including hardened calcifications. Ideally, such catheter devices would be sufficiently thin and flexible to be advanced through narrow, tortuous vasculature, such as the coronary vasculature, while also being configured to enhance the usable life of the ultrasound transmission wire within the catheter. Such devices would preferably provide sufficient longitudinal vibration of a distal catheter head for disrupting calcific plaque and other occlusions, while minimizing stress to the ultrasound transmission member or wire caused by transverse vibration.

BRIEF SUMMARY OF THE INVENTION

Ultrasound catheter devices and methods of the present invention provide enhanced disruption of blood vessel obstructions. Generally, an ultrasound catheter includes an elongate flexible catheter body with one or more lumens. An ultrasound transmission member or wire extends longitudinally through the catheter body lumen, and, in many embodiments, a guide wire tube also extends through the same lumen. A distal head is fixed to or otherwise mechanically coupled with the distal end of the ultrasound transmission member or wire and is positioned adjacent the distal end of the catheter body. Although the distal end of the catheter body often overlaps the distal head, the distal head is not directly affixed to the distal end of the catheter body. Thus, the distal tip may move freely (or "float"), relative to the distal end of the catheter body when ultrasonic energy is applied through the ultrasound transmission member.

A free-floating distal head enhances the ability of an ultrasonic catheter to disrupt vascular occlusions by using ultrasonic energy more efficiently. Basically, less energy is required to vibrate a floating distal head in a longitudinal direction for disrupting an occlusion. By using less ultrasonic energy, fewer unwanted transverse vibrations are created, thus reducing stress and fatigue of the ultrasound transmission member and increasing catheter longevity. The increased efficiency of such a free-floating head ultrasound catheter may be used to effectively disrupt calcific intravascular occlusions. In many embodiments, the distal end of the catheter body will overlap at least a portion of the distal head, to impart stability to the free-floating head.

In one aspect of the present invention, an ultrasound catheter for disrupting occlusions in blood vessels includes an elongate flexible catheter body having a proximal end, a distal end and at least one lumen. The catheter also includes an ultrasound transmission member extending longitudinally through the lumen of the catheter body, the ultrasound transmission member having a proximal end connectable to a separate ultrasound generating device and a distal end terminating adjacent the distal end of said catheter body. Finally, the catheter includes a distal head coupled with the distal end of the ultrasound transmission member, the distal head being positioned adjacent, but not directly affixed to, the distal end of the catheter body. Typically, the distal head is indirectly coupled with the catheter body, but only at a location proximal to the distal end of the body. In some embodiments, for example, the distal head is indirectly coupled to the catheter body via the guide wire tube, as described immediately below.

Optionally, the ultrasound catheter may also include a guide wire tube, having a lumen, that extends longitudinally through at least a portion of the lumen of the catheter body and extends longitudinally through the distal head. In some embodiments, such guide wire tube is affixed to the distal head and may also be affixed to the catheter body at a position proximal to the distal head. In some embodiments, for example, the guide wire tube is affixed to the catheter body at a location approximately 25 cm from the distal end of the catheter body. In other embodiments, the guide wire tube is affixed at a location approximately 25 cm from the distal end and at another location within approximately 1 cm from the distal end. Also optionally, the catheter may include a polymer sleeve disposed around a portion of the distal head, wherein the sleeve is coupled with the guide wire tube through a small hole in the distal head.

Generally, the distal head of the catheter may be fabricated from any suitable material, including but not limited to a metal or a polymer. In some embodiments, the distal head includes one or more radiopaque markers to improve its visibility via radiographic techniques.

Additionally, the distal head may have any suitable configuration. In some embodiments, the tip is a bulbous member formed on the distal end of the ultrasound transmission member. In many embodiments, the distal end of the catheter body overlaps at least a portion of the distal head. For example, the distal head may include a bulbous distal portion with a diameter approximately equal to the outer diameter of the catheter body and which extends beyond the distal end of the catheter body, and a proximal portion having a diameter smaller than the diameter of the distal portion, the proximal portion fitting within, but not affixed to, the distal end of the catheter body. In other embodiments, the distal head is fully positioned within the distal end of the lumen of the catheter body. In yet another embodiment, the distal end of the catheter body abuts a proximal end of the distal head, the distal head having a diameter approximately equal to the outer diameter of the catheter body.

Optionally, ultrasound catheters may also include a distal sleeve, coupled with the catheter body within the lumen of the catheter body. Such a sleeve will typically comprise a hollow, cylindrical member that surrounds a portion of the ultrasound transmission member. The sleeve enhances stability of the catheter when the catheter is twisted or torqued by a physician during use. For additional safety, some embodiments include an anchor member disposed within the lumen of the catheter body. The anchor member will generally have a distal end coupled with the distal head and a proximal end coupled with the catheter body. In some embodiments, the anchor will comprise a wire.

The ultrasound transmission member will typically be formed of a metal alloy. In many embodiments, such metal alloy is a superelastic metal alloy. Ultrasound transmission members will often benefit from some form of cooling mechanism. Therefore, many embodiments of the invention will include at least one fluid outlet port located near the distal end of the catheter body, the fluid outlet port being in fluid communication with the at least one lumen of the catheter body. This will allow fluid to be injected into the proximal end of the lumen so that it may pass longitudinally through the lumen and out of the at least one fluid outlet port. Such fluid may be used to cool the ultrasound transmission member.

In various embodiments, the catheter body of the ultrasound catheter will include only one lumen, which allows passage of the ultrasound transmission member, a guide wire tube, and any fluids or other substances infused through the catheter. In other embodiments, additional lumens may be included, such as a cooling fluid lumen adjacent the ultrasound transmission member.

Generally, the ultrasound catheter apparatus will include a proximal end connector assembly, coupled with the proximal end of the catheter body, for connecting the catheter to an ultrasound source. In one embodiment, such a connector assembly includes an elongate rigid body coupled with the proximal end of the catheter body and having a hollow bore, the hollow bore being communicative with at least one lumen of the catheter body, wherein the ultrasound transmission member extends proximally from the catheter body through at least a portion of the hollow bore. This embodiment of the assembly also includes one or more absorber members disposed within the hollow bore encircling the ultrasound transmission member, for absorbing transverse vibrations. The assembly also includes a sonic connector apparatus on the proximal end of the proximal end connector assembly for connection of the ultrasound transmission member to a separate ultrasound emitting device such that ultrasonic energy may be transmitted through the ultrasound transmission member to the distal head.

The proximal end connector assembly may also include one or more fluid inlet apertures, often in the form of a Y-connector with a side-arm, for infusing fluid through the Y connector and into the lumen of the catheter body. Another Y-connector side-arm may be included to allow introduction of a guide wire into the lumen of the catheter.

In many embodiments, the ultrasound transmission member includes one or more tapered regions near its distal end. For example, in some embodiments one or more tapered regions divide the ultrasound transmission member into a proximal portion and a distal portion. In many embodiments, the proximal portion has a larger diameter than the distal portion. Also in many embodiments, the distal portion of the ultrasound transmission member has a greater cross-sectional diameter than the tapered region, to enhance coupling of the distal portion of the member to the distal head. The tapered regions of transmission member generally provide it with enhanced flexibility.

Optionally, the ultrasound transmission member may include a metal wire having a friction-reducing coating formed around it. The coating, for example, may be composed of a polymeric material, such as polytetrafluoroethylene or polyethylene. In other embodiments, the coating may be comprised of a tubular jacket surrounding at least a portion of the ultrasound transmission member. In any case, the coating or jacket may cover the entire longitudinal length or less than the entire length of the ultrasound transmission member.

In another aspect of the invention, a method for disrupting a vascular occlusion includes positioning an ultrasonic catheter device adjacent the vascular occlusion and transmitting ultrasonic energy to the distal head to disrupt the vascular occlusion. As described above, the ultrasonic catheter device will typically include: an elongate flexible catheter body having a proximal end, a distal end and at least one lumen; an ultrasound transmission member extending longitudinally through the lumen of the catheter body, the ultrasound transmission member having a proximal end connectable to a separate ultrasound generating device and a distal end terminating adjacent the distal end of said catheter body; and a distal head coupled with the distal end of the ultrasound transmission member, the distal head being positioned adjacent, but not directly affixed to, the distal end of the catheter body.

Typically, positioning the ultrasonic catheter device will include passing the device over a guide wire. Additionally, as described above, the method will often include infusing one or more fluids through at least one fluid inlet aperture in the catheter body to a location adjacent the vascular occlusion. Such infusions may be used to cool the ultrasound transmission member or for any other suitable purpose.

BRIEF DESCRIPTION OF THE DRAWINGS

FIG. 1 is a perspective view of an ultrasound catheter device and ultrasound energy source according to an embodiment of the present invention.

FIG. 2 is a cross-sectional side view of a distal end of an ultrasound catheter device according to an embodiment of the present invention.

FIG. 2a is a front view of an ultrasound catheter device as in FIG. 2.

FIG. 2b is a partial cut-away perspective view of an ultrasound transmission member with a friction reducing coating or jacket according to an embodiment of the present invention.

FIG. 3 is a cross-sectional view of a distal end of an ultrasound catheter device according to another embodiment of the present invention.

FIG. 7 is a cross-sectional view of a proximal connection assembly of an ultrasound catheter device according to an embodiment of the present invention.

FIG. 7a is an exploded side view of a proximal connection assembly as in FIG. 4.

DETAILED DESCRIPTION OF THE INVENTION

Figure 4:
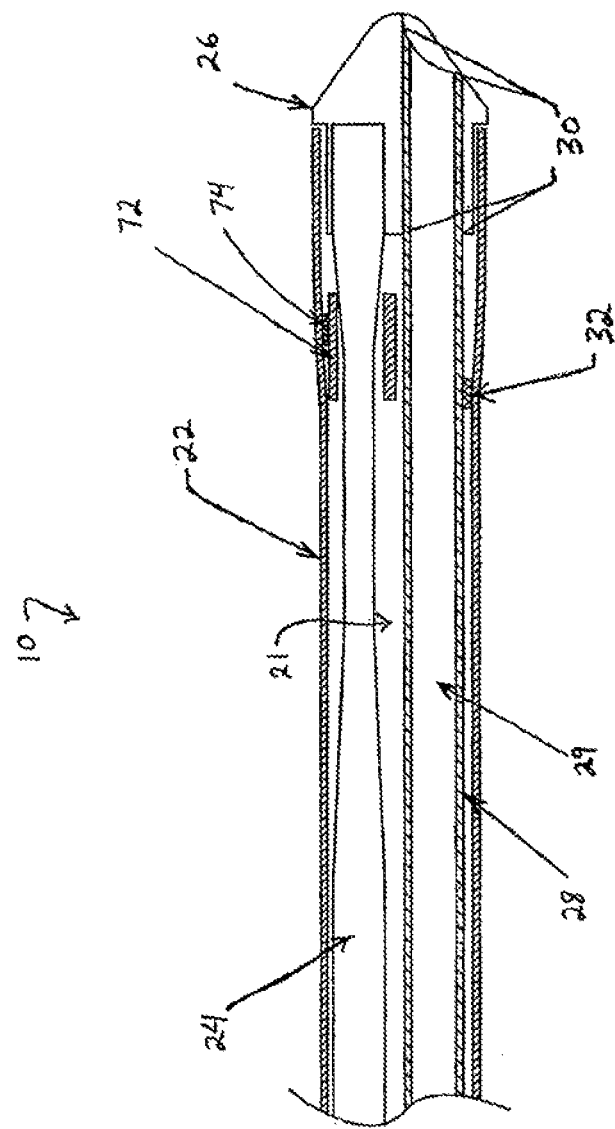
FIG. 4 is a cross-sectional view of a distal end of an ultrasound catheter device according to another embodiment of the present invention.

Ultrasound catheter devices and methods of the present invention generally provide for ablation and disruption of intravascular occlusions, including calcified occlusions. An ultrasound energy transmission member, such as a wire, typically transmits energy from an ultrasound transducer to a distal head of the catheter. The transmitted energy causes the distal head to vibrate, and such vibrational energy may be used to ablate vascular occlusions. Typically, the distal head of the ultrasound catheter is not directly affixed to the catheter body, which allows the distal head to move freely (or "float"), relative to the distal end of the catheter body. This freedom of movement generally provides increased energy transmission efficiencies, with reduced stress on the ultrasound transmission wire and, therefore, less wear and tear and premature breakage of the wire. Additionally, an unaffixed distal head may provide greater ablative capabilities, so that calcified occlusions may be disrupted.

Referring now to FIG. 1, one embodiment of an over-the-wire ultrasound catheter apparatus 20 suitably includes an ultrasound catheter 10, a proximal end connector assembly 12 coupled with catheter 10, an ultrasound transducer 14 coupled with the proximal end of proximal connector assembly 12, and an ultrasound generator 16 with a foot-actuated on/off switch 18, which is operatively coupled with ultrasound transducer 14 to provide ultrasonic energy to transducer 14 and, thus, to ultrasound catheter 10. Generally, catheter 10 will include an ultrasound transmission member, or wire (not shown), for transmitting energy from the transducer 14 to a distal head 26 of the catheter.

Proximal connector assembly 12, described more fully below, may have a Y-connector 15 with one or more side-arms 13, for example for providing irrigation fluid via an irrigation tube 11, or for passage of a guide wire. In other embodiments, as shown in FIG. 1, catheter 10 may be passed along a guide wire 17 which accesses catheter 10 via a side aperture, rather than a Y-connector side-arm.

It should be emphasized that ultrasound catheters 10 of the present invention may be used with any suitable proximal devices, such as any suitable ultrasound transducer 14 or ultrasound generator 16. Therefore, exemplary FIG. 1 and any following descriptions of proximal apparatus or systems for use with ultrasound catheters 10 should in no way be interpreted to limit the scope of the present invention as defined in the appended claims.

Referring now to FIG. 2, a cross-sectional side view of the distal end of one embodiment of ultrasound catheter 10 is shown. Generally, ultrasound catheter 10 suitably includes an elongate catheter body 22 with at least one hollow catheter body lumen 21. In FIG. 2, catheter body 22 is shown having one lumen, but it may have any number of lumens in various embodiments. Disposed longitudinally within catheter body lumen 21 are an ultrasound transmission member 24 and a hollow guide wire tube 28 forming a guide wire lumen 29. Coupled with the distal ends of ultrasound transmission member 24 and guide wire tube 28 is a distal head 26, positioned adjacent the distal end of catheter body 22.

Generally, the various coupled components described above may be coupled by any suitable means, such as adhesives, complementary threaded members, pressure fittings, and the like. For example, distal head 26 may be coupled with ultrasound transmission member 24 and guide wire tube 28 with any suitable adhesive substance. In one embodiment, for example, guide wire tube 28 is coupled with distal head 26 by means of adhesive at multiple head/guide wire adhesive points 30. In some embodiments, guide wire tube 28 may also be coupled with catheter body 22 by adhesive or other means at one or more body/guide wire adhesive points 32.

Catheter body 22 is generally a flexible, tubular, elongate member, having any suitable diameter and length for reaching a vascular occlusion for treatment. In one embodiment, for example, catheter body 22 preferably has an outer diameter of between about 0.5 mm and about 5.0 mm. In other embodiments, as in catheters intended for use in relatively small vessels, catheter body 22 may have an outer diameter of between about 0.25 mm and about 2.5 mm. Catheter body 22 may also have any suitable length. As discussed briefly above, for example, some ultrasound catheters have a length in the range of about 150 cm. However, any other suitable length may be used without departing from the scope of the present invention. Examples of catheter bodies similar to those which may be used in the present invention are described in U.S. Pat. Nos. 5,267,954 and 5,989,208, which were previously incorporated herein by reference.

In most embodiments, ultrasound transmission member 24, wire, or wave guide extends longitudinally through catheter body lumen 21 to transmit ultrasonic energy from ultrasound transducer 14, connected to the proximal end of catheter 10, to the distal end of catheter 10. Ultrasound transmission member 24 may be formed of any material capable of effectively transmitting ultrasonic energy from ultrasound transducer 14 to the distal end of catheter body 22, including but not necessary limited to metals such as titanium or titanium or aluminum alloys.

In accordance with one aspect of the invention, all or a portion of ultrasound transmission member 24 may be formed of one or more materials which exhibit superelastic properties. Such material(s) should preferably exhibit superelasticity consistently within the range of temperatures normally encountered by ultrasound transmission member 24 during operation of ultrasound catheter apparatus 10. Specifically, all or part of the ultrasound transmission member 24 may be formed of one or more metal alloys known as "shape memory alloys".

Use of superelastic metal alloys in ultrasound transmission members is described in U.S. Pat. No. 5,267,954, previously incorporated by reference. Examples of superelastic metal alloys which may be used are described in detail in U.S. Pat. No. 4,665,906 (Jervis); U.S. Pat. No. 4,565,589 (Harrison); U.S. Pat. No. 4,505,767 (Quin); and U.S. Pat. No. 4,337,090 (Harrison). The disclosures of U.S. Pat. Nos. 4,665,906; 4,565,589; 4,505,767; and 4,337,090 are expressly incorporated herein by reference insofar as they describe the compositions, properties, chemistries and behavior of specific metal alloys which are superelastic within the temperature range at which the ultrasound transmission member of the present invention operates, any and all of which superelastic metal alloys may be used to form ultrasound transmission member 24 of the present invention.

In many embodiments, ultrasound transmission member 24 includes one or more tapered regions 23 along a portion of its length, towards its distal end. Such a tapered region 23 decreases the distal rigidity of ultrasound transmission member 24, thus amplifying ultrasound energy transmitted along ultrasound transmission member 24 to distal head 26. Tapered region 23 typically divides the transmission member 24 between a proximal portion and a distal portion, which both typically have a larger cross-sectional diameter than tapered region 23, as pictured in FIG. 2. A thicker distal portion, for example, may enhance stability of the connection between ultrasound transmission member 24 and distal head 26. Other embodiments are contemplated, however. For example, tapered region 23 may be positioned at the extreme distal end of transmission member 24. In still other embodiments, ultrasound transmission member 24 may include multiple tapered portions, widened portions and/or the like. Thus, ultrasound transmission member 24 may be configured with any suitable length, combinations of diameters and tapers, or any other suitable shapes, sizes or configurations to advantageously transmit ultrasound energy from transducer 14 to distal tip 26.

With reference now to FIG. 2*b*, in some embodiments, ultrasound transmission member 24 may include a low-friction coating or jacket 25 on all or a portion of its outer surface. Coating 25 may be disposed on the outer surface of ultrasound transmission member 24 so as to completely cover ultrasound transmission member 24 along its entire length, or along a discrete region or regions thereof. Such coating or jacket 25 may comprise a layer of low friction polymer material such as polytetrafluoroethylene (PTFE), TEFLON™ (available from Dupont, Inc., Wilmington, Del.) or other plastic materials such as polyethylene. Coating 25 may be applied as a liquid and subsequently allowed to cure or harden on the surface of ultrasound transmission member 24. Alternatively, coating 25 may be in the form of an elongate tube, disposable over the outer surface of ultrasound transmission member 24. Generally, coating 25 serves to prevent or diminish friction between the outer surface of ultrasound transmission member 24 and the adjacent structures of catheter 10 or proximal end connector assembly 12 through which ultrasound transmission member 24 extends.

In most embodiments, distal head 26 is mounted on or otherwise coupled with the distal end of ultrasound transmission member 24. In many embodiments, as shown in FIG. 2, distal tip includes a proximal region 27 with an outer diameter configured to fit within the distal end of catheter body lumen 21 and a distal region 29 with a slightly larger diameter than proximal region 27. In many embodiments, all or a portion of distal region 29 of distal head 26 will have an outer diameter approximately the same as the outer diameter of catheter body 22. Thus, in embodiments like the one pictured in FIG. 2, the distal end of catheter body 22 overlaps at least a portion of distal head 26. The amount of overlap may vary in different embodiments, so that in some embodiments, catheter body 22 may completely overlap distal head 26. This overlapping may enhance stability of the distal end of catheter 10 and distal head 26 in particular.

In another embodiment, as shown in FIG. 3, distal head 34 is configured so that its proximal end-abuts the distal end of catheter body 22. In this embodiment, distal head 26 is held in position adjacent catheter body 22 by its attachment to ultrasound transmission member 24 and/or guide wire tube 28 and does not fit within catheter body lumen 21. Typically, in such an embodiment, all or a portion of distal head 34 will have an outer diameter that is approximately equal in dimension to the outer diameter of catheter body 22.

As is evident from distal heads 26 and 34, shown in FIGS. 2 and 3, distal heads may have any suitable configuration, shape, and size suitable for ablating or otherwise disrupting occlusions. For example, distal head 26, 34 may have a shape that is bulbous, conical, cylindrical, circular, rectangular, or the like. Similarly, distal head 26, 34 may have dimensions which allow it to fit wholly or partially within the distal end of catheter body lumen 21 or may, alternatively, be disposed completely outside catheter body lumen 21. Thus, the configuration of distal head 26 may take any suitable form and should in no way be limited by the exemplary embodiments pictured in FIGS. 2 and 3 and described above or below.

Distal head 26 is not directly affixed to the distal end of catheter body 22. Instead, in various embodiments, it is held in place by its attachment to either ultrasound transmission member 24, guide wire tube 28, or both. In some embodiments, distal head 26 may additionally be secured to the distal end of catheter body 22 by fitting partially or wholly within catheter body lumen 21, as described above, but distal head 26 will not be affixed to catheter body 22 with adhesive, complementary threaded members, other connective devices or the like. Thus, distal head 26 will be able to move freely, relative to the distal end of catheter body 22. Positioning distal head 26 in this way, without affixing it to catheter body 22, allows greater freedom of movement of head 26, providing enhanced efficiency of ultrasound energy transmission and reduced stress to ultrasound transmission member 24.

Typically, distal head 26 is actually coupled indirectly with the catheter body at one or more points, but only at a location proximal to the distal end of catheter body 22. In some embodiments, for example, distal head 26 is indirectly coupled to the catheter body 22 via guide wire tube 28, as described immediately below. For example, distal head 26 may be coupled with guide wire tube 28, and guide wire tube 28 may be coupled with catheter body 22 at a location within 1 cm of the distal end of catheter body 22, at a location around 25 cm from the distal end of catheter body 22, or at any other location or combination of locations. In other embodiments, distal head 26 may be coupled with ultrasound transmission member 24, and ultrasound transmission member 24 may be coupled with catheter body 22 near its proximal end and/or at any other suitable location.

In some embodiments, distal head 26 is formed of radiodense material so as to be easily discernable by radiographic means. For example, distal head 26 may be formed of a metal or metal alloy. Alternatively, distal head 26 may be made of a polymer or ceramic material having one or more radiodense markers affixed to or located within distal head 26. In one embodiment, for example, distal head 26 may be molded of plastic such as acrylonitrile-butadiene-styrene (ABS) and one or more metallic foil strips or other radiopaque markers may be affixed to such plastic distal head 26 in order to impart sufficient radiodensity to permit distal head 26 to be readily located by radiographic means. Additionally, in embodiments wherein distal tip 26 is formed of molded plastic or other non-metallic material, a quantity of radiodense filler such as powdered bismuth or BaSO$_4$ may be disposed within the plastic or other non-metallic material of which distal head 26 is formed so as to impart enhanced radiodensity to distal head 26.

Typically, guide wire tube 28 will also be disposed longitudinally within catheter body lumen 21, along all or a portion of the luminal length. In most embodiments, guide wire tube 28 will also extend through distal head 26, as shown in FIGS. 2 and 3. It should be understood, however, that guide wire tube 28 and guide wire lumen 29 may be given any suitable configuration, length, diameter and the like suitable for passing catheter 10 along a guide wire to a location for treatment. For example, in some embodiments, a relatively short guide wire lumen 29 may be formed near the distal end of catheter body 22 to permit rapid exchange of guide wires and catheters. In some embodiments, guide wire lumen 29 may be accessed via a side-arm 13 on a Y-connector 15, while in other embodiments guide wire lumen 29 may be accessed via a guide wire aperture in a side wall of catheter body 22. Thus, catheters 10 of the present invention are not limited to those including guide wire tubes 28 and or guide wire lumens 29 as described by FIGS. 2 and 3.

In many embodiments, guide wire tube 28 is attached to both distal head 26 and catheter body 22. As previously described, such attachment may be accomplished by any suitable means, such as by an adhesive substance. Generally, guide wire tube 28 is attached within a portion of distal head 26 at one or more adhesive points 30. An outer wall of guide wire tube 28 also may be attached to an inner wall of catheter body 22 at one or more guide wire tube/catheter body adhesive points 32. For example, in some embodiments tube/catheter body adhesive point 32 is located approximately 25 cm from the distal end of catheter body 22. Other embodiments may include one tube/catheter body adhesive point at approximately 25 cm from the distal end of catheter body 22 and another tube/catheter body adhesive point within approximately 1 cm of the distal end of catheter body 22. Any suitable adhesive point or combination of multiple adhesive points is contemplated.

Such attachment of guide wire tube 28 to both distal head 26 and catheter body 22 helps to hold distal head 26 in its position at the distal end of catheter body 22. Attachment also helps limit unwanted transverse motion of distal head 26 while allowing longitudinal motion due to tube elasticity. Adhesives used to attach guide wire tube 28 to distal head 26 and catheter body 22 may include, but are not limited to cyanoacrylate (e.g. Loctite™, Loctite Corp., Ontario, CANADA; or Dron Alpha™, Borden, Inc., Columbus, Ohio) or polyurethane (e.g. Dymax™ Dymax Engineering Adhesive, Torrington, Conn.) adhesives.

In still other embodiments, a portion of distal head 26 may be formed to extend laterally wider than the outer surface of catheter body 22 and guide wire tube 28 may be positioned on the outer surface of catheter body 22. Such embodiments, wherein guide wire tube 28 is positioned along the outer surface of catheter body 22, are commonly referred to as "monorail" catheters, as opposed to "over-the-wire" catheters as described by FIGS. 2 and 3. In addition to over-the-wire embodiments and monorail embodiments, ultrasound catheter 10 may also be configured as a combination or hybrid of over-the-wire and monorail embodiments. Specifically, such embodiments may include an ultrasound catheter 10 having a guide wire tube 28 formed through a distal portion of catheter body 22 only, with a guide wire entry/re-entry aperture being formed through a sidewall of catheter body 22 to permit passage of a guide wire from the distal guide wire lumen of the catheter to a position outside the catheter body.

With reference now to FIG. 2*a*, some embodiments of ultrasound catheter 10 include one or more fluid outflow apertures 36 in distal head 26 to permit fluid flow out of catheter body lumen 21. Other embodiments (not shown) may include one or more similar apertures at or near the distal end of catheter body 22, either in addition to or in place of apertures 36 in distal head 26. Outflow apertures 26 facilitate continual or intermittent passage of coolant liquid through lumen 21, for example by infusion into lumen 21 via one or more side-arms 11, 13. Infusion of coolant liquid through lumen 21, in proximity to ultrasound transmission member 24, may be used to control the temperature of ultrasound transmission member 24 to prevent overheating during use. Cooling liquids may include, but are not limited to, saline and the like.

In some embodiments, guide wire tube 28 and lumen 29 are generally configured with an inner diameter slightly larger than the outer diameter of a guide wire along which catheter 10 is passed. Such a guide wire tube 28 may then be used as an alternative or additional means to allow fluid outflow through distal head 26. In still other embodiments, one or more separate lumens having separate outflow apertures formed at or near the distal tip of the catheter may be formed for infusion of oxygenated perfusate, medicaments or other fluids into the blood vessel or other anatomical structure in which the catheter is positioned.

Referring now to FIG. 4, some embodiments of ultrasound catheter 10 include a distal sleeve 72 which is coupled with catheter body 22 and which surrounds a portion of ultrasound transmission member 24. Generally, distal sleeve 72 comprises a hollow cylindrical member, made of any suitable material, such as but not limited to a polymer. Sleeve 72 is coupled with catheter body 22 within lumen 21 at a location near the distal end of catheter body 22. Sleeve 72 may be coupled with body 22 via any reasonable means but will often by coupled via an adhesive at one or more adhesive points 74, such as those described above for coupling other components of catheter 10.

By surrounding a portion of ultrasound transmission member 24 and being coupled with catheter body 22, distal sleeve 72 adds stability to catheter 10. Although it is not necessary for use of catheter 10 and does not enhance the performance of catheter 10, physicians often twist or torque catheters radially upon insertion and/or during use of a catheter. Such twisting motions may cause guide wire tube 28 to kink and/or collapse as the tube 28 moves in relation to catheter body 22 and transmission member 24. Placement of distal sleeve 72 around transmission member 24 causes the components of catheter 10 to move together when catheter 10 is twisted, thus avoiding kinking or collapsing of guide wire tube 28 and maintaining patency of guide wire lumen 29.

Figure 5:
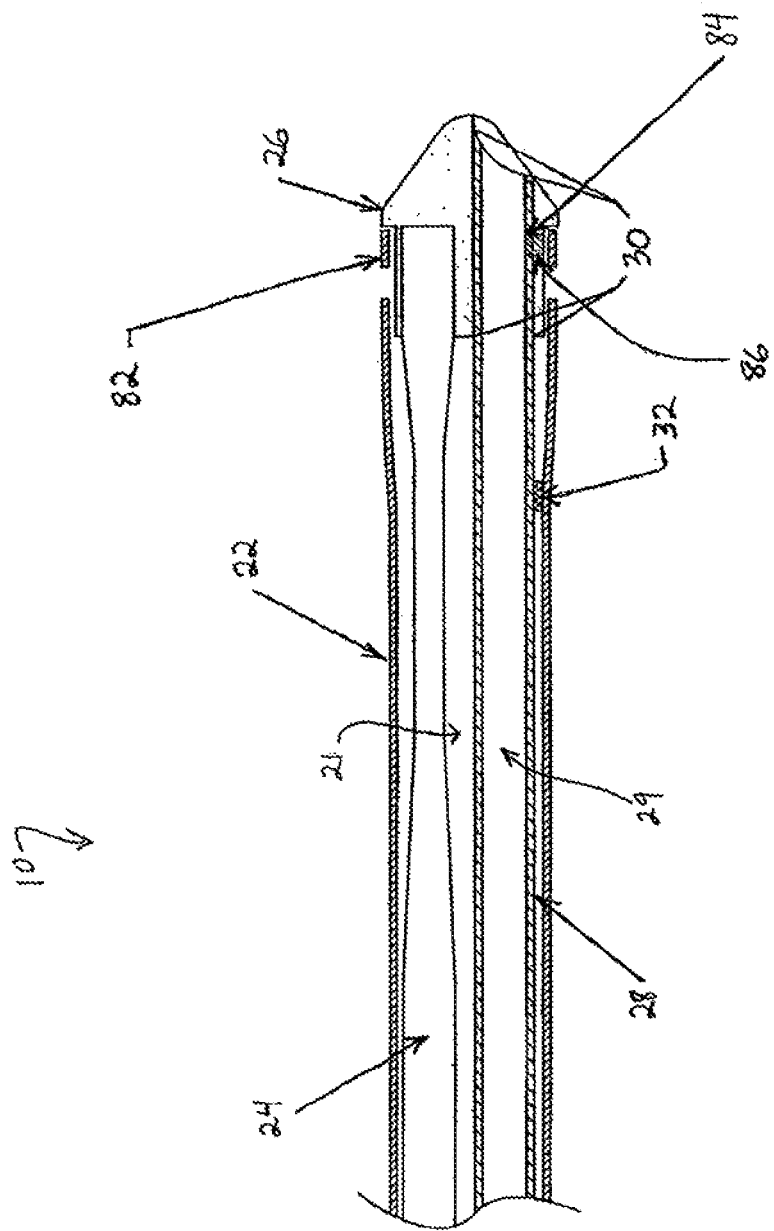
FIG. 5 is a cross-sectional view of a distal end of an ultrasound catheter device according to another embodiment of the present invention.

Referring now to FIG. 5, another embodiment of ultrasound catheter 10 includes a distal head sheath 82. Distal head sheath 82 is generally a cylindrical sheath that surrounds a portion of distal head 26. Sheath 82 is coupled with guide wire tube 28 via an adhesive at an adhesive point 84, which is accessed through a small hole 86 in a side portion of distal head 26. Sheath 82 may be made of any suitable material, but will typically be made of a polymer of the same or similar material with which guide wire tube 28 is made. Securing sheath 82 to tube 28 through hole 86 in distal head 26, enhances the stability of the connection between tube 28 and distal head 26. Thus, there is less chance that distal head 26 will break off from catheter 10 and safety of the device is enhanced. Forming sheath 82 and guide wire tube 28 from the same or similar materials will allow for a secure connection between the two via an adhesive.

Figure 6:
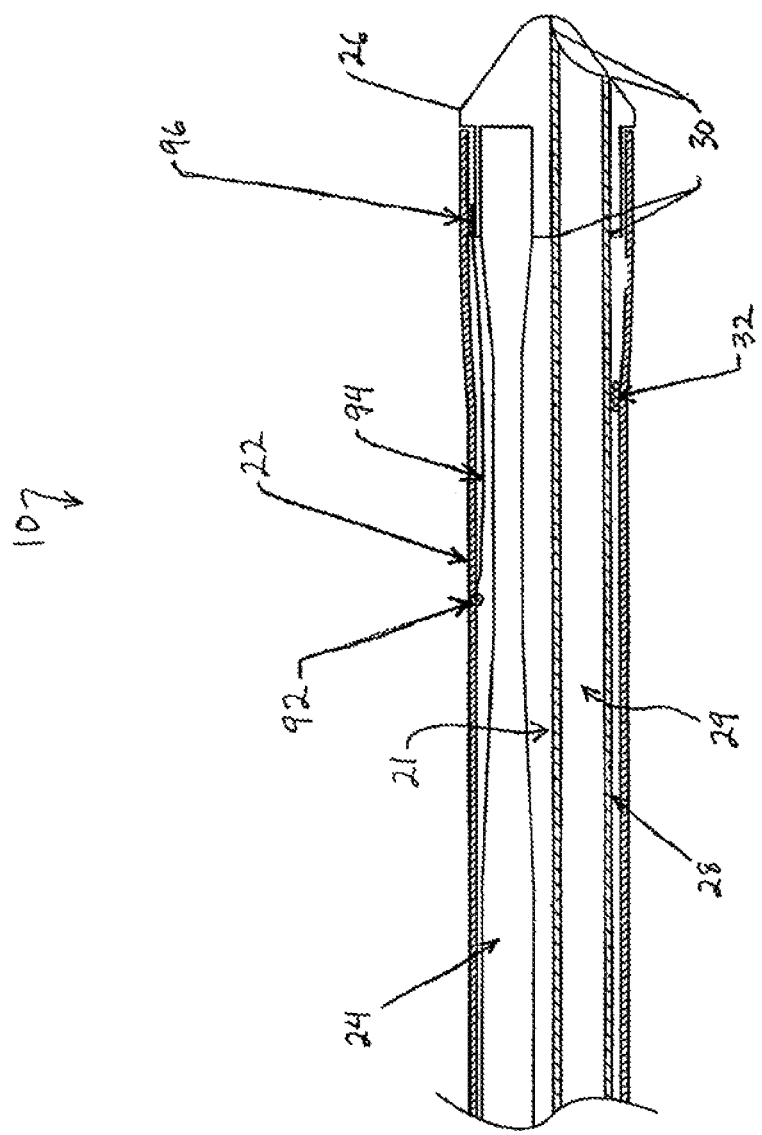
FIG. 6 is a cross-sectional view of a distal end of an ultrasound catheter device according to another embodiment of the present invention.

With reference now to FIG. 6, yet another embodiment of catheter 10 includes a distal head anchor 94. Distal head anchor 94 may comprise a wire or similar device made from metal, polymer or any other suitable material. Generally, a distal portion of anchor 94 is coupled with distal head 26 at an adhesive point 96, and a proximal portion of anchor 94 is coupled with catheter body 22 at an adhesive point 92 proximal to the extreme distal end of catheter body 22. Therefore, distal head 26 remains free-floating relative to the extreme distal end of catheter body 22 but is anchored to catheter body 22 at a more proximal location 92. This anchoring helps ensure that distal head 26 will not break off from catheter 10 during use. Any suitable anchoring device may be used and is contemplated within the scope of the invention.

Various types and designs of proximal end connector apparatus 12, ultrasound transducers 14, ultrasound generation devices 16 and/or the like may be coupled with ultrasound catheter 10 for use of catheter 10 to disrupt vascular occlusions. Detailed descriptions of such apparatus may be found, for example, in U.S. Pat. Nos. 5,267,954 and 5,380,274, invented by the inventor of the present invention and previously incorporated herein by reference. Therefore, the ultrasound catheters apparatus 20 and methods are not limited to use with any particular transducers 14, ultrasound generators 16, connector apparatus 12 or the like.

That being said, and with reference now to FIG. 7, one embodiment of proximal end connector apparatus 12 suitably includes a housing 42 with a hollow inner bore 44. Bore 44 may have a uniform inner diameter along its length or, alternatively, may have multiple segments, such as a proximal segment 47, a middle segment 45 and a distal segment 49, each of which may surround one or more various components of proximal end connector apparatus 12.

Generally, proximal segment 47 of bore 44 is configured to allow attachment to ultrasound transducer 56, via transducer housing 58 and transducer thread 54. As such, proximal segment 47 includes a proximal portion of sonic connector 48, including a sonic connector thread 52 for connection with complementary transducer thread 54. Proximal segment 47 and/or the proximal end 41 of housing 42 may have any shape, diameter or configuration to allow coupling with transducer housing 58. As shown in FIG. 7, proximal segment 47 may have an inner diameter of a size to allow transducer housing 58 to fit within it. Thus, transducer housing 58 and proximal end 41 may be coupled via a pressure fit. In other embodiments, transducer housing 58 and proximal end 41 may connect via complementary threads. In still other embodiments, transducer housing 58 may fit around the outer diameter of proximal end 41. It should be apparent that any suitable configuration of proximal end may be used.

Similarly, sonic connector thread 52 may have any suitable size, shape and configuration for coupling with a complementary transducer thread 54. Such coupling may be achieved via complementary threads, snap-fit mechanism, or any other suitable means. Otherwise, sonic connector thread 52 and sonic connector 48 are generally configured to transmit ultrasound energy from ultrasound transducer 56 to ultrasound transmission member 24. A pin 50 is generally positioned within sonic connector 48 and is disposed between proximal segment 47 and middle segment 45 of bore 44.

Middle segment 45 of bore 44 typically surrounds a portion of sonic connector 48, which is coupled with the distal end of ultrasound transmission member 24, and one or more sets of absorber members 46, which surround a portion of ultrasound transmission member 24 to reduce vibration of member 24. Absorber members 46 may include, for example, one or more 0-rings. Sonic connector 48 is coupled with the distal end of ultrasound transmission member 24 by any suitable means, to transmit ultrasound energy to member 24 from transducer 56.

Absorber members 46 are configured to circumferentially surround ultrasound transmission member 24 in whole or in part to dampen transverse vibrations created by the transmission of ultrasound energy. The number, size and configuration of absorber members 46 used may be determined based upon a desired level of dampening and any suitable configuration or combination may be used. Alternatively, other dampening structures may be used, rather than absorber members 46, and thus the configuration of proximal connector apparatus 12 is not limited to the use of one or more sets of absorber members 46.

Distal segment 49 of bore 44 typically surrounds a portion of ultrasound transmission member 24 and may also contain one or more additional sets of absorber members 46. Distal segment 49 may also contain a portion of a Y-connector 15, which is coupled with the distal end 43 of housing 42 of proximal end connector apparatus 12. Again, coupling of Y-connector 15 with distal end 43 of apparatus 12 may be accomplished via complementary threads, pressure fitting, or any other suitable means. A Y-connector lumen 45 of Y-connector 15 allows passage of ultrasound transmission member 24 and is in communication with catheter body, lumen 21.

Y-connector 15 may have one or more side-arms 11 to allow passage of a guide wire, infusion of a cooling fluid or any other suitable fluid, or passage of any other suitable structure or substance from side-arm 11, through Y-connector 15, to catheter 10. In some embodiments, a lumen of side-arm 11 is in fluid communication with Y-connector main lumen 45 and catheter body lumen 21. In other embodiments, side-arm 11 may have a lumen that communicates with a separate lumen in Y-connector 15 and catheter body 22.

Generally, pressurized fluid such as a coolant liquid may be infused through side-arm 11, through Y-connector lumen 45 and through catheter body lumen 21 so that it flows out of fluid outflow apertures 36. The temperature and flow rate of such coolant liquid may be specifically controlled to maintain the temperature of ultrasound transmission member 24 at a desired temperature within its optimal working range. In particular, in embodiments of the invention wherein ultrasound transmission member 24 is formed of a metal alloy which exhibits optimal physical properties (e.g. super elasticity) within a specific range of temperatures, the temperature and flow rate of coolant liquid infused through fluid infusion side-arm 11 may be specifically controlled to maintain the temperature of ultrasound transmission member 24 within a range of temperatures at which it demonstrates its most desirable physical properties. For example, in embodiments of the invention wherein ultrasound transmission member 24 is formed of a shape memory alloy which exhibits super elasticity when in its martensitic state, but which loses super elasticity as it transitions to an austenite state, it will be desirable to adjust the temperature and flow rate of the coolant liquid infused through fluid infusion side-arm 11 so as to maintain the shape memory alloy of ultrasound transmission member 24 within a temperature range at which the alloy will remain in its martensitic state and will not transition to an austenite state. The temperature at which such shape memory alloys transition from a martensitic state to an austenite state is known as the "martensitic transition temperature" of the material. Thus, in these embodiments, the fluid infused through side-arm 11 will be at such temperature, and will be infused at such rate, as to maintain the shape memory alloy of ultrasound transmission member 24 below its martensitic transition temperature.

Referring now to FIG. 7a, proximal end connector apparatus 12 is shown in exploded side view. In this embodiment, sonic connector 48 is held within housing 42, by means of dowel pin 50. In other embodiments, dowel pin 50 may not be included and sonic connector 48 may be positioned within housing by other means. Otherwise, FIG. 4a simply demonstrates the various components previously described with reference to FIG. 4;

Although the invention has been described above with specific reference to various embodiments and examples, it should be understood that various additions, modifications, deletions and alterations may be made to such embodiments without departing from the spirit or scope of the invention. Accordingly, it is intended that all reasonably foreseeable additions, deletions, alterations and modifications be included within the scope of the invention as defined in the following claims.

What is claimed is:

1. A catheter comprising:
   a body with proximal and distal ends comprising a lumen;
   a first fluid outflow aperture disposed in the body;
   a second fluid outflow aperture disposed in the body;
   an ultrasound transmission member disposed in the lumen wherein the member is movable;
   a head connected to the member; and
   a guidewire tube at least partially disposed inside the lumen extending to the head, the guidewire tube coupled to the body at a location wherein movement of the member imparts movement to the head.

2. The catheter of claim 1 wherein the location is between the distal end and the first fluid outflow aperture.

3. The catheter of claim 2 wherein the first fluid outflow aperture is located distally of the second fluid outflow aperture.

4. The catheter of claim 3 wherein the guidewire tube is coupled to the body at a second location.

5. The catheter of claim 4 wherein the second location is between the distal end and the second fluid outflow aperture.

6. The catheter of claim 5 further comprising a proximal-end connector assembly coupled with the proximal end.

7. The catheter of claim 6 wherein the second fluid outflow aperture is in fluid communication with the lumen.

8. The catheter of claim 6 wherein the head is adjacent the distal end.

9. The catheter of claim 6 wherein the head is disposed partially within the distal end.

10. The catheter of claim 4 wherein the second location is between a proximal end of the head and the second fluid outflow aperture.

11. The catheter of claim 2 wherein the head is disposed partially within the distal end.

12. The catheter of claim 1 wherein the head is adjacent the distal end.

13. The catheter of claim 1 wherein the head is disposed partially within the distal end.

14. A catheter comprising:
 an elongate body comprising a lumen and having a distal end;
 an ultrasound transmission member disposed within the lumen wherein the member is movable;
 a head coupled to the member and disposed inside the lumen; and
 a guidewire tube at least partially disposed inside the lumen extending through at least a portion of the lumen and extending through the head, wherein longitudinal movement of the member imparts longitudinal movement to the head.

15. The catheter of claim 14 wherein a proximal end of the head has a larger cross-sectional diameter than a distal-most end of the head.

16. The catheter of claim 15 wherein the distal end of the body overlaps at least part of the head.

17. The catheter of claim 15 wherein the head is disposed partially within the distal end.

18. The catheter of claim 14 wherein the head is disposed partially within the distal end.

19. The catheter of claim 1 wherein the location is between the proximal end and the first fluid outflow aperture.

* * * * *